Sept. 29, 1964 M. L. THOMPSON Plant Pat. 2,448
ROSE PLANT
Filed Oct. 2, 1963
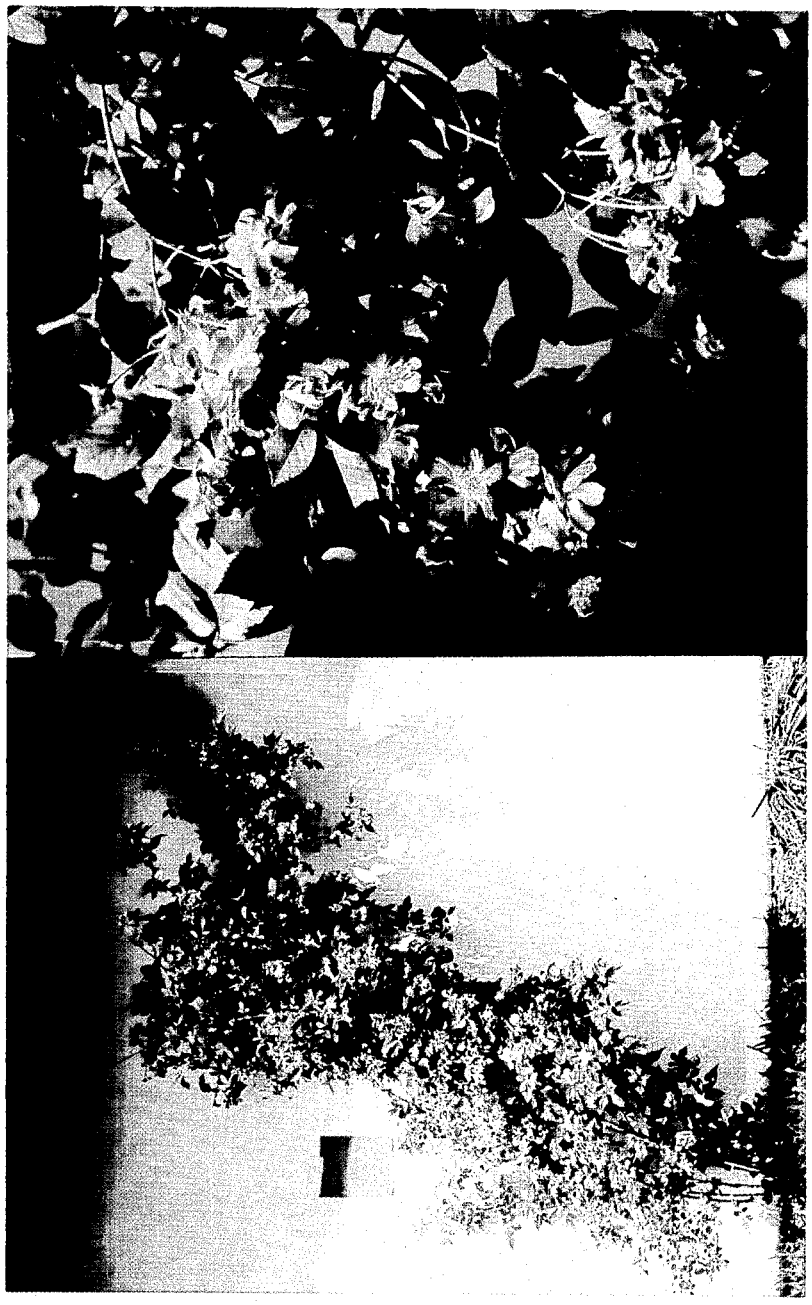
Inventor.
Mary Lea Thompson
By: Robb & Robb
Attorneys United States Patent Office Plant Pat. 2,448
Patented Sept. 29, 1964

2,448
ROSE PLANT
Mary Lea Thompson, Tyler, Tex.
(Rte. 1, Box 221, Van, Tex.)
Filed Oct. 2, 1963, Ser. No. 313,404
1 Claim. (Cl. Plt.—2)

The present invention relates to a new and distinct variety of rose plant of the climber class, which was discovered by me on cultivated property in Tyler, Texas, as a newly found rose variety of unknown parentage, but which presumably originated as a chance seedling.

At the time of my initial discovery of this new variety, I was visiting at the home of an elderly couple in Tyler, Texas. During the course of my visit, I came across the new variety referred to above, which apparently had been growing without any particular significance to the owners of the property.

At the time of my discovery, my attention was attracted to this new variety by the extremely unusual coloring of the flowers borne thereby. The flowers ranged in color from light blue or lavender as the flowers first opened, to a very deep blue or dark purple, often approaching navy blue in the more mature flowers. I was accordingly so intrigued with this unusual flower color in a rose variety that I requested permission of the owners to take cuttings from the original plant, whose parentage was completely unknown. Being granted this permission, I rooted a number of cuttings on my own property and kept the plants and flowers derived therefrom under close and continuous observation for a number of years. These observations have convinced me that the new variety is quite unique in the class of climbing roses. In its habit of growth and blooming period, it generally resembles the well-known variety "Paul's Scarlet" (unpatented), but the flowers are only about one-half the size of those of this variety, and are of an entirely different color.

These factors, among others summarized in the following, definitely differentiate this newly found variety from all other varieties of which I am aware, and constitute a unique combination in which the following features are particularly outstanding:

(1) Vigorous and hardy habits of growth;

(2) Abundant production of small, flat, open flowers which are usually borne several to a stem; and (3) A distinctive and attractive general color tonality of the flowers corresponding to light blue or lavender-violet in the early stages, but deepening to navy blue or very dark purple, with a yellow center, as the flowers open fully and mature.

Asexual reproduction of the new variety, as performed by me by own-rooted cuttings on my property in Tyler, Texas, has fully confirmed the novel characteristics and distinctions referred to above, and has established that these characteristics and distinctions come true to form and are transmissible through succeeding propagations.

The accompanying drawing shows a typical climbing plant of my new rose variety, as well as typical specimens of the flowers and foliage on a somewhat enlarged scale, all as depicted in color as nearly true as it is reasonably possible to make the same in a color illustration of this character.

The following is a detailed description of my new variety, with color terminology in accordance with Nickerson's Color Fan, published by Munsell Color Company, Inc., of Baltimore, Maryland, except where general color terms of ordinary dictionary significance are obvious, as based upon observations of specimens grown outdoors in Tyler, Smith County, Texas.

Parentage: Newly found variety of unknown parentage.
Type: Hardy; climbing; outdoor; for garden decoration.
Classification: Climber.

*Flower*

Blooming habit: Blooms for about three weeks annually, similar to "Paul's Scarlet."
Fragrance: Slight.
Flowers borne: Several to stem; on stems of medium length and normal strength.
Quantity of bloom: Abundant, outdoors.
Bud:
- *Peduncle.*—Medium length. Color—green.
- *Before calyx breaks.*—Size—small. Form—pointed-oval.
- *As calyx breaks.*—Color—Light Violet, Plate 10PB 6/8 or Strong Reddish Purple, Plate 10P 5/10, with some being very Strong Purplish Blue, Plate 7.5PB 4/10.
- *As first petal opens.*—Size—small. Color—from Strong Purple, Plate 5P 4/9 to Deep Purplish Blue, Plate 7.5PB 3/10.
- *Opening.*—Opens up well.

Bloom:
- *Size (when fully open).*—Small; from 1 to 2 inches in diameter.
- *Petalage.*—Double; usually about 20 petals per flower; petals are obovoid and notched.
- *Form.*—Flat; open.
- *General color tonality.*—Ranges from Light Purplish Blue, Plate 7.5PB 7/7 or Brilliant Violet, Plate 10PB 5/9 in early stages, deepening to Deep Purplish Blue, Plate 7.5PB 3/10, with Vivid Yellow, Plate 5Y 8/12 center, as flowers open fully and mature; petals have a pale yellow area at extreme base; upper and lower petal surfaces are substantially the same colors.
- *Behavior.*—Drop off cleanly.
- *Flower longevity.*—On bush in garden—5 days in April. Cut roses grown outdoors and kept at living-room temperatures—6 days in April.

*Reproductive Organs*

Stamens: Few. Color—yellow.
Filaments: Short.
Anthers: Small.
Hips: Very short; elliptical. Color—green.
Sepals: Falling soon; slightly fringed; reflexed outwardly.
Seeds: Few; small.

*Plant*

Foliage:
- *Leaves.*—Compound of 3–5 leaflets; normal abundance; thick, soft texture.
- *Leaflets.*—Shape—oval, with apex acute. Base—round. Margin—simply serrate.
- *Color.*—Upper surface—medium green. Under surface—light green.
- *Rachis (the supporting stem of the compound leaf).*—Light. Upper side—smooth. Under side—mostly smooth, but with a few prickles.
- *Stipules.*—Medium length.

Growth:

*Habit.*—Climbing.

*Growth.*—Vigorous.

*Canes.*—Medium caliper.

*Main stems.*—Color—green. Thorns—few; hooked downward; with round base.

*Branches.*—Color—green. Thorns—few; hooked downward.

*New shoots.*—Color—green.

I claim:

A new and distinct variety of rose plant of the climber class, substantially as herein shown and described, characterized particularly as to novelty by the unique combination of vigorous and hardy habits of growth, abundant production of small, flat, open flowers usually borne several to stem, and a distinctive and attractive general color tonality of the flowers ranging from light blue or lavender-violet in the early stages and deepening to very dark purple to substantially navy blue with yellow center as the flowers fully open and mature.

No references cited.